United States Patent
Kröning et al.

(10) Patent No.: US 8,037,764 B2
(45) Date of Patent: Oct. 18, 2011

(54) DEVICE AND METHOD FOR THE MATERIAL TESTING AND/OR THICKNESS MEASUREMENTS OF A TEST OBJECT THAT CONTAINS AT LEAST FRACTIONS OF ELECTRICALLY CONDUCTIVE AND FERROMAGNETIC MATERIAL

(75) Inventors: Michael Kröning, Saarbrücken (DE); Jorj Nichiforenco, Saarbrücken (DE); Andrei Boulavinov, Saarbrücken (DE)

(73) Assignee: Fraunhofer-Gesellschaft zur Förderung Der Angewandten Forschung e.V., Munich (DE)

( * ) Notice: Subject to any disclaimer, the term of this patent is extended or adjusted under 35 U.S.C. 154(b) by 584 days.

(21) Appl. No.: 11/718,609

(22) PCT Filed: Nov. 3, 2005

(86) PCT No.: PCT/EP2005/011782
§ 371 (c)(1),
(2), (4) Date: Jan. 13, 2009

(87) PCT Pub. No.: WO2006/048290
PCT Pub. Date: May 11, 2006

(65) Prior Publication Data
US 2009/0139335 A1    Jun. 4, 2009

(30) Foreign Application Priority Data
Nov. 5, 2004 (DE) .......................... 10 2004 053 584

(51) Int. Cl.
*G01N 29/04* (2006.01)
*G01N 27/90* (2006.01)
(52) U.S. Cl. ................ 73/643; 73/592; 73/622; 73/627; 324/238

(58) Field of Classification Search .................. 73/643, 73/592, 620, 622, 623, 625, 627–629, 866.5; 324/238
See application file for complete search history.

(56) References Cited

U.S. PATENT DOCUMENTS
5,608,164 A * 3/1997 MacLauchlan .............. 73/599
(Continued)

FOREIGN PATENT DOCUMENTS
DE         35 11 676 A1    10/1985
(Continued)

OTHER PUBLICATIONS
M. Gori et al, "EMAT Transducers and Thickness Characterization on Aged Boiler Tubes", Ultrasonics 34, 1996, pp. 339-343.

*Primary Examiner* — J M Saint Surin
(74) *Attorney, Agent, or Firm* — Antonelli, Terry, Stout & Kraus, LLP.

(57) ABSTRACT

The invention relates to a device and a method for testing the material of a test object (4) which contains at least electrically conductive and ferromagnetic material fractions and has at least one engineered surface (5), by means of at least one electromagnetic ultrasonic transducer assembly (EMUS). Said assembly comprises a permanent or electromagnetic assembly (1) comprising at least two magnetic poles (N, S) of different magnetic polarity that face the engineered surface (5), in addition to an eddy current coil (2) that is placed in close proximity to the engineered surface (5) between the two magnetic poles (N, S) in indirect or direct relation to the engineered surface (5). The invention is characterized in that the eddy current coil (2) is configured and arranged in such a way that when said coil (2) is supplied with an alternating current, free ultrasonic waves that run essentially perpendicular to the engineered surface (5) are generated and propagate inside the test object (4).

35 Claims, 3 Drawing Sheets

U.S. PATENT DOCUMENTS

| | | | | |
|---|---|---|---|---|
| 5,619,423 A | * | 4/1997 | Scrantz | 702/51 |
| 5,987,993 A | * | 11/1999 | Meier et al. | 73/643 |
| 6,009,756 A | * | 1/2000 | Willems et al. | 73/643 |
| 7,024,935 B2 | * | 4/2006 | Paige et al. | 73/643 |
| 7,426,867 B2 | * | 9/2008 | Koch et al. | 73/627 |

FOREIGN PATENT DOCUMENTS

| | | |
|---|---|---|
| DE | 195 43 481 A1 | 5/1997 |
| EP | 0 781 994 A2 | 7/1997 |
| WO | WO 97/05469 | 2/1997 |
| WO | WO 2004/007138 A1 | 1/2004 |

* cited by examiner

DEVICE AND METHOD FOR THE MATERIAL TESTING AND/OR THICKNESS MEASUREMENTS OF A TEST OBJECT THAT CONTAINS AT LEAST FRACTIONS OF ELECTRICALLY CONDUCTIVE AND FERROMAGNETIC MATERIAL

BACKGROUND OF THE INVENTION

1. Field of the Invention

The invention pertains to a device and a method for the material testing of a test object that contains at least fractions of electrically conductive and ferromagnetic material and features at least one engineered surface with at least one electromagnetic ultrasonic transducer assembly (EMUS) that comprises a permanent or electromagnetic assembly with at least two magnetic poles of different magnetic polarity that face the engineered surface, as well as at least one eddy current coil that is arranged in a projection on the engineered surface between the two magnetic poles in indirect or direct relation to the engineered surface.

2. Description of the Prior Art

It is common practice to utilize electromagnetic ultrasonic transducers for nondestructive material testing and for measuring test objects that consist of electrically conductive materials and preferably also have ferromagnetic properties.

One can distinguish between two types of electromagnetic ultrasonic transducers, namely those that make it possible to generate so-called horizontally polarized shear waves that predominantly propagate within the test object parallel to the coupling surface and US-transducers for generating so-called freely propagating ultrasonic waves that predominantly propagate within the test object perpendicular to the coupling surface. In both instances, the stimulation of ultrasonic waves within the test object can be attributed to magnetostrictions and Lorentz forces produced by the presence of a magnetic field that is largely constant over time in superposition with an electromagnetic alternating field caused by an electric alternating current.

Figure 5:
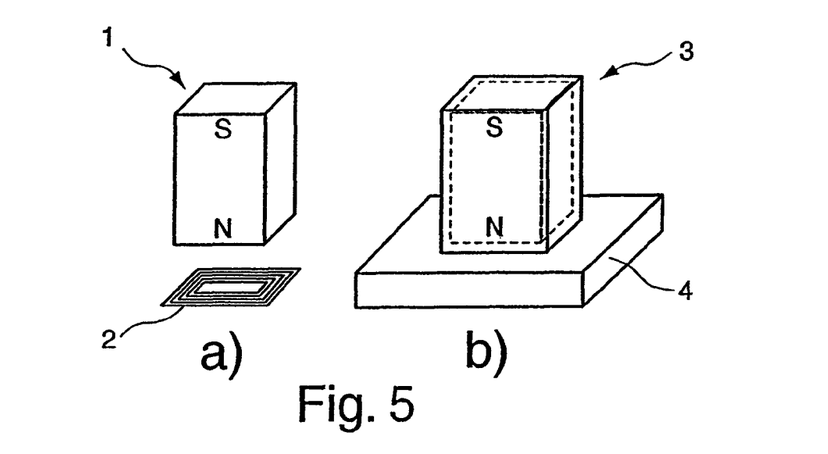

A typical setup for stimulating ultrasonic waves in accordance with the so-called EMUS-principle is shown in FIGS. 5 *a* and *b*. Conventional EMUS-transducers 3 feature a permanent magnet 1 as well as an eddy current coil 2 that are realized in the form of one unit and therefore can be jointly operated. The eddy current coil 2 is typically realized in the form of a rectangular or flat spiral coil and arranged on the side of one magnetic pole of the permanent magnet 1 such that the coil 2 is perpendicularly permeated by a permanent magnetic field. If the aforementioned EMUS-transducer 3 is placed on an electrically conductive, ferromagnetic test object 4, the permanent magnetic field and a circuital vector field caused by the eddy current coil are superimposed within the test object such that magnetostrictive effects are induced therein due to the superposition of the magnetic field components of the circuital vector field and the permanent magnetic field that permeates the surface of the test object perpendicularly, wherein Lorentz forces are also generated by the eddy currents induced in the test object such that pressure waves which normally occur perpendicular to the test object surface are ultimately generated in the form of radially polarized shear waves that are able to propagate within the test object in the form of ultrasonic waves. According to the state of the art, both wave types, that is, the ultrasonic waves propagating perpendicular to the test object surface and the ultrasonic waves that propagate parallel to the test object surface due to the radially polarized shear waves, are suitable for use in checking for defects such as, for example, the detection of cracks within the test object, as well as in measuring the wall thickness of the test object.

Since the eddy current coils currently in use are highly sensitive to external mechanical influences, it should be attempted to generally protect such coils from mechanical wear. When examining ferromagnetic test objects, this is further complicated, in particular, in that the eddy current coil situated between the permanent magnet and the test object is literally pressed onto the surface of the test object due to the attractive effect of the magnetic forces and thusly subjected to significant frictional wear.

In this context, German Patent 35 11 076 A1 discloses a pig for electromagnetically testing pipeline walls of steel that makes it possible to examine and detect weak spots caused by corrosion on pipeline walls during the course of a nondestructive test. One pig that is described in greater detail in this publication features electromagnets that are uniformly distributed over the circumference and respectively feature two measuring heads that are axially aligned with one another, a yoke that connects the measuring heads and a magnetizing coil on these measuring heads. In this case, the field of each electromagnet extends parallel to the central pipe axis. The ultrasonic measurements are realized by directly arranging an eddy current coil that is acted upon with strong current pulses having very steep edges on at least one of the poles or magnet heads. Round seams are provided at the junctions of two adjacent pipeline sections and subject the electromagnetic transducer to impact stress when the aforementioned pig travels over the seams as part of a continuous inspection, wherein this impact stress is substantially amplified by the magnetic forces acting between the electromagnets and the pipeline wall. The above-described frictional wear as well as the additional impact stress on the electromagnetic ultrasonic transducer, particularly on the eddy current coil, results in short service lives of EMUS-transducers that should be extended.

Although it is possible to reduce the frictional wear by diminishing the magnetic forces of attraction acting between the EMUS-transducer and the test object to be examined, for example, by lowering the magnetic field induction, this measure would simultaneously result in a substantially lower efficiency of the EMUS-transducer, that is, the force density induced within the test object in order to generate the ultrasonic waves is reduced correspondingly such that the detection sensitivity during the reception of scattered or reflected ultrasonic waves is diminished accordingly.

Another electromagnetic ultrasonic transducer disclosed in European Patent 0 781 994 A2 utilizes two separate eddy current coils for the transmission and the reception to and from an electrically conductive, ferromagnetic test object, wherein said eddy current coils are preferably arranged congruently and provided with an intermediate insulating layer. FIG. 17 of the cited publication shows an EMUS-transducer in which a permanent magnetic field is generated by means of a U-shaped permanent magnet, both magnetic poles of which face a test object to be examined. The eddy current coils that respectively serve for generating as well as for receiving ultrasonic waves and are realized in the form of meander-type coils lie between the surface regions of the test object that is spanned by the U-shaped permanent magnet in a bridge-like fashion. Due to the meander-shaped configuration of the strip conductors, the current directions of two strip conductor sections that extend directly adjacent to one another are oriented opposite to one another. This results in eddy current regions that lie directly adjacent to one another within the test object and generate Lorentz forces with diametrically different directions in superposition with a permanent magnetic field near the surface that is directed parallel to the test object, wherein these Lorenz forces may, in turn, produce pressure waves in the form of horizontally polarized shear waves that propagate along the surface of the test object in the form of ultrasonic waves. Such ultrasonic waves that propagate parallel to the test object surface are well suited for the material testing near the surface, but cannot be used for depth or thickness measurements on the test objects.

SUMMARY OF THE INVENTION

The invention is a device and a method for the material testing of test objects that contain at least fractions of an electrically conductive and ferromagnetic material on the basis of electromagnetic ultrasonic stimulation, namely such that it is ensured that the eddy current coils required for generating eddy currents are only subjected to slight frictional wear, if any, and the test object can be examined over its entire depth or thickness and thickness measurements can be carried out. The measures to be taken should be suitable, in particular, for examining and measuring tubular as well as disk-shaped test object geometries.

A device for the material testing of a test object in accordance with the invention contains at least fractions of electrically conductive and ferromagnetic material and features at least one engineered surface with at least one electromagnetic ultrasonic transducer assembly that comprises a permanent or electromagnetic assembly with at least two magnetic poles of different magnetic polarity that face the engineered surface, as well as at least one eddy current coil that is arranged in a projection on the engineered surface between the two magnetic poles in indirect or direct relation to the engineered surface, wherein the at least one eddy current coil is configured and arranged such that free ultrasonic waves that essentially propagate within the test object perpendicular to the engineered surface are generated when the eddy current coil is supplied with an alternating current.

The device in accordance with the invention makes it possible to position the least one eddy current coil relative to the engineered surface of the test object independently of the magnetic forces of attraction acting between the permanent or electromagnetic assembly and the test object such that it is not subjected to any frictional wear as it would occur when the eddy current coil is pressed against the engineered surface of the test object to be examined under the influence of the magnetic forces. The eddy current coil is arranged relative to the engineered surface of the test object in a region that is permeated by a tangential magnetic field originating from the magnetic poles that are arranged along the engineered surface and spaced apart from one another, that is, the magnetic field lines that permeate the test object and originate from the permanent or electromagnetic assembly extend largely parallel to the engineered surface, on or relative to which the eddy current coil is arranged. In contrast to conventional EMUS-transducers in which the eddy current coil is directly arranged on the magnetic pole surface such that it faces a test object, no forces of attraction induced by external magnetic fields act between the eddy current coil and the test object to be examined when using the device of the invention. Depending on the respective embodiment, it is possible to rigidly connect the at least one eddy current coil with the permanent or electromagnetic assembly if a suitable holding arrangement is provided. Such a fixed spatial allocation between the permanent or electromagnetic assembly and the at least one eddy current coil makes it possible to handle the electromagnetic ultrasonic transducer assembly according to the invention in a simple and coordinated fashion. However, the independent handling of the permanent or electromagnetic assembly and the at least one eddy current coil may be advantageous for certain applications, for example in instances in which the permanent or electromagnetic assembly is arranged on one side of the test object to be examined and the at least one eddy current coil is arranged on the side of the test object that lies opposite of the permanent or electromagnetic assembly, namely in such a way that the at least one eddy current coil is always positioned between the two magnetic poles of the permanent or electromagnetic assembly in a projection on the engineered surface. In all possible embodiments, it must be observed that the tangential magnetic field that originates from the permanent or electromagnetic assembly and permeates the test object parallel to the engineered surface is superimposed or interacts with the circuital vector field induced within the test object by the eddy current coil being supplied with an alternating current. It also needs to be ensured that the tangential magnetic field induced in the test object extends to a sufficient depth or, in other words, that this magnetic field is also prevalent in the test object region in which the circuital vector field is induced by the eddy current coil, particularly in instances in which the permanent or electromagnetic assembly and the at least one eddy current coil are respectively arranged on opposite sides of the test object as described above.

Special eddy current coils need to be provided and suitably oriented relative to the tangential magnetic field in order to generate free ultrasonic waves that essentially propagate within the test object perpendicular to the engineered surface. It is important to utilize the at least one eddy current coil for creating a three-dimensional region within the test object, in which an eddy current with a higher current density and a uniform eddy current direction is induced, namely in the region of the tangential magnetic field. In more precise terms, it is important to realize and arrange the at least one eddy current coil relative to the test object permeated by the tangential magnetic field in such a way that a region is created within the test object that is spatially defined by the geometry of the eddy current coil and in which a resultant circuital vector field is induced that has a higher eddy current density than the surrounding regions and a uniform eddy current direction. It is also important to simultaneously orient the eddy current direction induced in the test object perpendicular to the magnetic field lines of the tangential magnetic field in the region of the increased eddy current density.

One preferred eddy current coil that fulfills the aforementioned requirements features an electric conductor arrangement that can be supplied with an alternating current and at least regionally or sectionally comprises at least two electric conductors that essentially extend parallel to one another and through which the alternating current flows and the same direction, preferably a multitude of such electric conductors. It is important to select eddy current coil assemblies in which pressure wave phenomena that compensate one another within the test object for the device of the invention in order to prevent that the ultrasonic waves generated by magnetostriction are destructively superimposed underneath the respective opposite coil sides due to their phase shift of 180 degrees as it is the case with a rectangular coil, in which the current flows through the opposite coil sides in opposite directions and in which the opposite coil sides are spatially situated close to one another due to a usually compact winding.

Two preferred variations of such an eddy current coil assembly are described in the following embodiments, wherein one variation represents a three-dimensional eddy current coil and the other variation features a two-dimensional strip conductor arrangement with at least two strip conductor sections that are configured analogous to a rectangular coil, wherein the strip conductor sections are arranged adjacent to one another in such a way that both rectangular coils are arranged directly adjacent to one another with one respective rectangular coil section, through which the alternating current flows in identical directions.

The inventive device is able to induce free ultrasonic waves that essentially propagate perpendicular to the engineered surface, opposite of which the electromagnetic ultrasonic transducer is arranged. Depending on the type of test object as well as its magnetic saturation, the induction of ultrasonic waves is based on the magnetostrictive effect or on Lorentz forces. Both mechanisms for inducing ultrasonic waves are described in greater detail below with reference to the figures.

The device of the invention is used in a method for the material testing of a test object that contains at least fractions of electrically conductive and ferromagnetic material by generating electromagnetic ultrasonic waves within the test object that features an engineered surface, wherein the method is characterized by the following steps. A magnetic field initially needs to be generated within the test object, wherein the magnetic field lines of this magnetic field are at least regionally oriented parallel to the engineered surface and form a so-called tangential magnetic field. In addition, an eddy current coil acted upon with an alternating current is located relative to the engineered surface in order to induce an alternating magnetic field in the test object, wherein the alternating field induced by means of the eddy current coil is superimposed with the tangential magnetic field. In this respect, it is important that both magnetic fields are respectively oriented such that their magnetic field lines extend parallel to one another, but not necessarily in the same direction.

Consequently, a resultant magnetic field that either results from the addition or the subtraction of both magnetic field intensities is formed within the region in which both magnetic fields are superimposed, namely in dependence on the orientation of the periodically changing direction of the magnetic field lines of the alternating field. Pressure waves are induced due to the magnetostrictive effect of the periodically changing resultant magnetic field within the test object, wherein these pressure waves cause the release of free ultrasonic waves that propagate within the test object perpendicular to the engineered surface. In addition, Lorentz forces are generated by the eddy currents induced in the test object and act in the region of the tangential magnetic field, wherein these Lorentz forces also generate pressure waves for the formation of free ultrasonic waves, the propagating direction of which is oriented perpendicular to the engineered surface. In the above-described constellation between the conventional magnetic field generated by the permanent or electromagnetic assembly and the eddy currents that can be generated with the eddy current coil, both effects contribute to the generation of free ultrasonic waves that are used for measuring and accordingly inspecting a test object over its entire depth.

Since the eddy current coil is preferably excited by the alternating current in a pulsed fashion, it is not only possible to carry out material testing, but also to measure wall thicknesses of test objects by means of transit time measurements. In this case, the transit times between the generation of ultrasonic waves and the reception of ultrasonic waves are measured, wherein the generated ultrasonic waves are reflected on a boundary surface or a surface of the test object, respectively.

The inventive device therefore is particularly suitable for measuring the thickness of tubular test objects such as, for example, pipelines as well as disk-shaped test objects, for example, wheels of rail vehicles.

According to one preferred embodiment, the inventive device is used as an integral component of a pig that is guided along the interior of a pipeline by means of a suitable drive, wherein the pipeline can be inspected for material defects and its wall thickness, in particular, can be measured without causing damages to the electromagnetic ultrasonic transducer. Additional details of other embodiments are provided in the following description.

BRIEF DESCRIPTION OF THE DRAWINGS

Embodiments of the invention are described below in an exemplary fashion with reference to the figures, namely without restricting the general scope of the invention to these particular embodiments.

FIGS. 2a and b show the principle of stimulating ultrasonic waves by means of the magnetostrictive effect as well as Lorentz forces;

FIGS. 4a and b schematic representations of an alternative eddy current coil;

FIGS. 5a and b show EMUS-transducers according to the state of the art;

DETAILED DESCRIPTION OF THE INVENTION

Different arrangements and configurations of the device in accordance with the invention are illustrated in FIGS. 1a to f. In order to test materials and, in particular, to measure the thickness of a test object 4 that consists of an electrically conductive and ferromagnetic material, the device features a U-shaped permanent magnet assembly 1 that spans over the test object 4 in a yoke-like fashion and directly contacts the engineered surface of the test object 4 on the face side with its magnetic poles N, S. As described further below, in particular, with reference to FIG. 2, the permanent magnet 1 induces a tangential magnetic field within the test object 4 in the region between the magnetic poles N, S, wherein this tangential magnetic field is constant over time if a permanent magnet 1 is used. Instead of providing the permanent magnet 1 illustrated in FIG. 1, it would also be possible to utilize an electromagnet of identical or similar configuration that is able to induce a tangential magnetic field that is variable over time in the test object 4. In this case, it needs to be ensured that the frequency of the alternating current required for generating the tangential magnetic field is substantially lower than the frequency of the alternating current supplied to the eddy current coil 2 arranged on the engineered surface 5 of the test object 4 in the region of the effective tangential magnetic field. For reasons of simplicity, it is furthermore assumed that the magnet assembly 1 is realized in the form of a permanent magnet of the type described above.

The supply of an alternating current to the eddy current coil 2 results in a circuital vector field being induced in the region of the test object in which the tangential magnetic field induced by the permanent magnet assembly 1 is prevalent. Free ultrasonic waves 6 that are coupled into the interior of the test object 4 perpendicular to the engineered surface 5 are generated due to the superposition of both fields, namely due to magnetostrictive effects as a well as the generation of Lorentz forces as described in greater detail below, in particular, with reference to FIG. 2. Among other things, the wall thickness of the test object 4 can be determined by means of a conventional pulse-echo transit time measurement on the engineered surface 5, wherein the transit time measurement is realized with the ultrasonic waves induced by means of the electromagnetic ultrasonic transducer principle. The various embodiments shown in FIGS. 1a to c illustrate the variability of the arrangement of the at least one eddy current coil 2 on the test object relative to the permanent magnet 1. In the arrangement according to FIG. 1b, the eddy current coil 2 is situated on the opposite surface of the test object 4 referred to the permanent magnet 1. In this case, it is important to ensure that the tangential magnetic field induced in the test object 4 by the permanent magnet 1 acts over the entire thickness of the test object 4. In the embodiment shown in FIG. 1c, the test object 4 is situated between the two magnetic poles N, S such that the tangential magnetic field forms over the entire length of the test object 4.

In order to measure and inspect large-surface test objects 4, it is possible to correspondingly utilize several eddy current coils as illustrated in the embodiments shown in FIGS. 1d and e.

FIG. 1f shows a schematic top view of the electromagnetic ultrasonic transducer assembly, for example according to FIG. 1a, and illustrates that the eddy current coil 2 can be moved parallel or transverse to the tangential magnetic field lines extending from the north pole to the south pole independently of the magnet assembly. If so required, an air gap between the eddy current coil 2 and the test object 4 can be correspondingly adjusted or varied if the surface is curved or contains uneven areas, for example, due to elevated welding seams, protruding seams, corrosion, dirt or the like.

Figure 1:
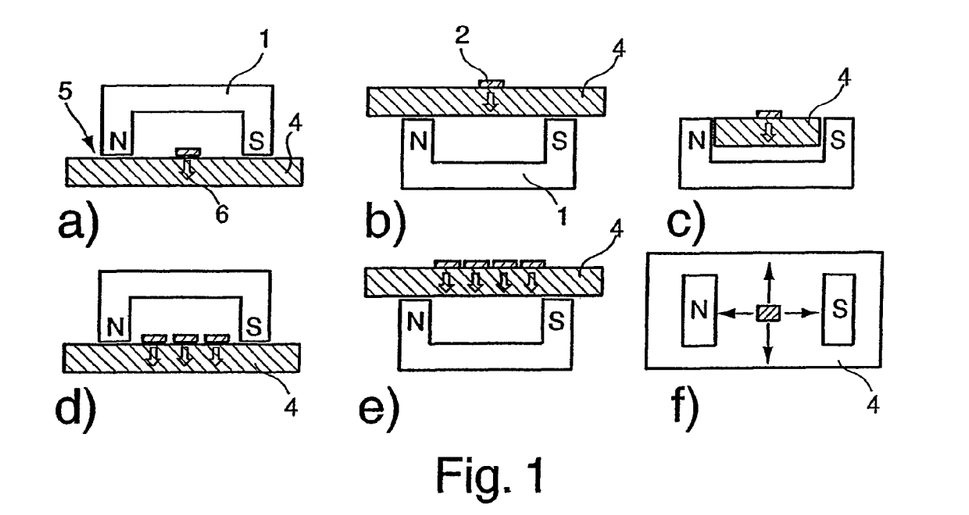
FIGS. 1a-f show different arrangements of an inventive EMUS-transducer relative to a test object.
Figure 2:
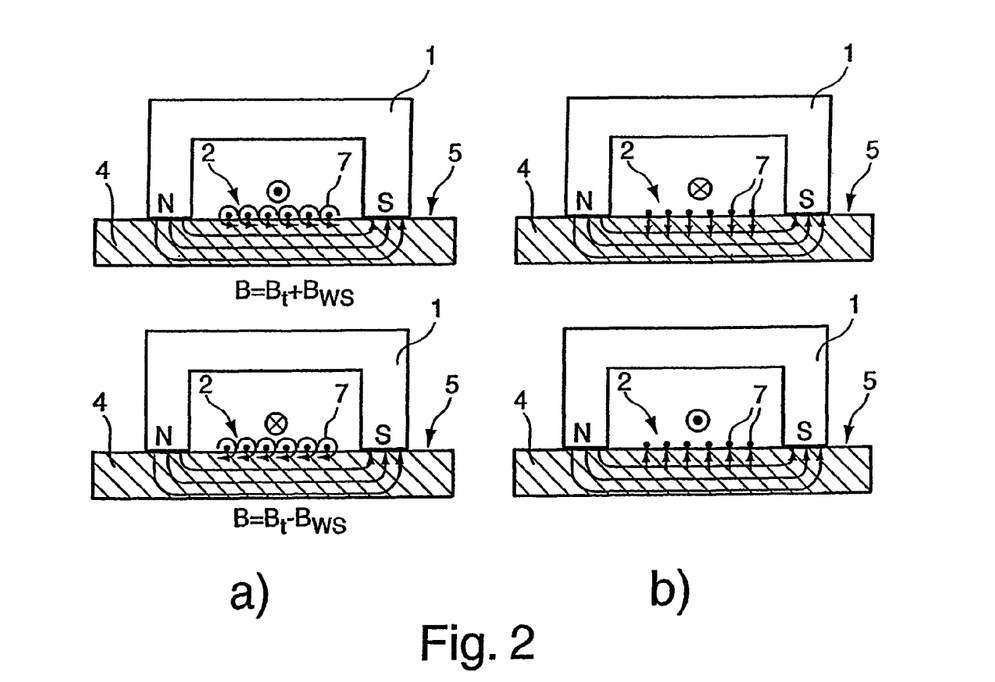

Certain measures that are described below with reference to FIG. 2 need to be taken in order to generate free ultrasonic waves that essentially propagate perpendicular to the engineered surface in the interior of the test object 4. In the embodiments shown in FIGS. 2a and b, a U-shaped permanent magnet 1 is provided for inducing a tangential magnetic field $B_T$ that is constant over time within the test object 4. It is furthermore assumed that the eddy current coil 2 is composed of a multitude of electric conductors 7 that extend parallel to one another and through which an alternating current respectively flows in the same current direction.

With respect to the situation illustrated in the upper portion of FIG. 2a, it is assumed that an electric current that is directed out of the plane of projection uniformly flows through the electric conductors 7 of the eddy current coil 2. The current flow generates an alternating magnetic field $B_{WS}$ that is constructively superimposed with the tangential magnetic field $B_T$ in the region of the test object. In this case, a resultant magnetic field B is formed at least in the region of the alternating magnetic field $B_{WS}$ induced within the test object 4 by the eddy current coil 2, wherein $B=B_T+B_{WS}$ applies to this resultant magnetic field.

In the situation illustrated in the lower portion of FIG. 2a, a current that is directed into the plane of projection uniformly flows through the electric conductors 7 of the eddy current coil 2. According to the preceding explanations, this results in a subtraction of the alternating magnetic field $B_{WS}$ from the tangential magnetic field $B_T$ that is constant over time. The resultant magnetic field in the region of the alternating magnetic field $B_{WS}$ generated by the eddy current coil 2 therefore can be expressed as follows: $B=B_T-B_{WS}$.

Based on the magnetostrictive effect, the resultant magnetic field B that changes over time generates ultrasonic waves that propagate into the test object 4 perpendicular to the engineered surface 5 in the form of transverse waves.

Additionally or alternatively to the generation of ultrasonic waves on the basis of the magnetostrictive effect, free ultrasonic waves are also generated by Lorentz forces acting within the test object, wherein this effect is, however, substantially weaker in ferromagnetic materials than that based on magnetostriction. The generation of ultrasonic waves on the basis of Lorentz forces is particularly suitable for generating longitudinal waves in non-ferromagnetic materials. A corresponding excitation mechanism is illustrated in FIG. 2b. In the upper illustration of FIG. 2b, it is assumed that a current directed into the plane of projection uniformly flows through the electric conductors 7 of the eddy current coil 2. This current flow generates eddy currents within the test object that are perpendicularly directed into the test object 4 in the described embodiment and superimposed with the tangential magnetic field $B_T$ such that Lorentz forces $F_L$ are generated. If the current flows through the electric conductors 7 in the opposite direction as illustrated in the lower portion of FIG. 2b, Lorentz forces $F_L$ are generated perpendicularly toward the engineered surface 5. It becomes evident that the alternating Lorentz forces $F_L$ are able to generate ultrasonic waves propagating perpendicular to the engineered surface in respectively opposite effective directions, namely in dependence on the direction of the alternating current.

The preceding description of excitation mechanisms for releasing free ultrasonic waves within the test object 4 make it clear that special eddy current coil assemblies need to be used for generating a higher current density with a preferred current direction that is essentially oriented perpendicular to the tangential magnetic field in a limited three-dimensional space within the test object. Corresponding alternative embodiments of such an eddy current coils are illustrated in FIGS. 3 and 4.

Figure 3:
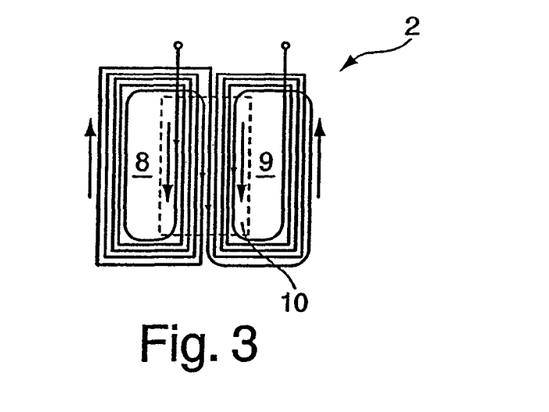
FIG. 3 shows a schematic top view of an inventive eddy current coil.
Figure 4:
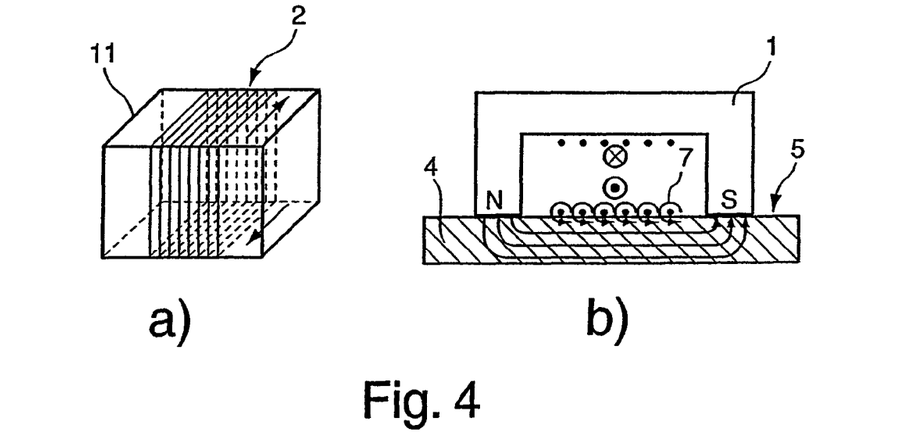

FIG. 3 shows a two-dimensional eddy current coil that features a strip conductor assembly resembling a butterfly wing. It has of two identical strip conductor sections 8 and 9 that are arranged adjacent to one another in such a way that both strip conductor sections realized in the form of rectangular coils are positioned directly adjacent to one another with one respective rectangular coil section, through which the alternating current respectively flows in the same direction (see the region bordered by broken lines as well as the arrows indicating the respective direction of the current flow). The region 10 situated within the border drawn with broken lines is the so-called working zone, in which the electric currents flowing through the electric strip conductor sections are always oriented identically. The eddy current density in the test object underneath the working zone 10 therefore is substantially higher than in other regions such that the generation of ultrasonic waves with this gradient is most favorable at this location or in this region, respectively.

FIGS. 4a and b show another alternative variation of a three-dimensional eddy current coil 2 for stimulating free ultrasonic waves. According to FIG. 4a, the electric conductor forming the eddy current coil 2 is wound around a cuboid coil frame 11. FIG. 4b shows a cross section through a thusly designed electromagnetic ultrasonic transducer, in which the U-shaped permanent magnet 1 protrudes over the cuboid eddy current coil 2. It is assumed that a current that is directed out of the plane of projection of FIG. 4b uniformly flows through the electric strip conductors 7 of the eddy current coil that are in direct contact with the engineered surface 5 of the test object 4. It is obvious that such a coil geometry only stimulates eddy currents in the test object with one coil side of the otherwise three-dimensional eddy current coil. In the embodiment shown, no oppositely oriented eddy currents that can compensate one another, for example, analogous to a conventional rectangular coil geometry are generated within the test object.

We refer to the preceding introduction of the description with respect to FIG. 5 that shows a conventional electromagnetic ultrasonic transducer.

Figure 6:
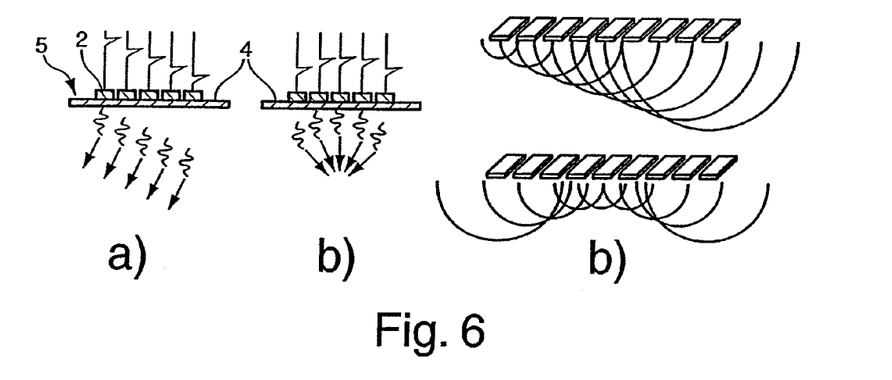
FIGS. 6a-c show schematic representations of the Phased-Array control of a multitude of eddy current coils.

The option of arranging a multitude of eddy current coils 2 relative to an engineered surface 5 of a test object 4 and for exciting these eddy current coils by means of a so-called Phased-Array control is discussed below with reference to FIGS. 6a, b and c. The initially mentioned magnet assembly 1 is not illustrated in order to provide a better overview. The Phased-Array principle is based on the phase-controlled excitation of the ultrasonic transducer that consists of several elements. For example, the ultrasonic beam emitted by all eddy current coils 2 can be respectively pivoted and focused by means of a sound field control. In case of the pivoted emission of the ultrasonic wave field illustrated in FIG. 6a, the individual eddy current coils 2 are controlled with a linear time delay. In case of the focusing shown in FIG. 6b, it is important to excite the individual eddy current coils in accordance with the law of parabolic deceleration. Both of the aforementioned excitation principles conform to the sound field according to Huygens principle as shown in FIG. 6c.

Figure 7:
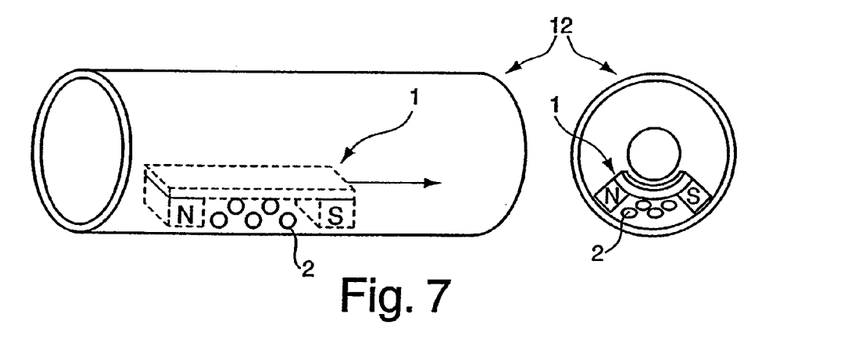
FIGS. 7 and 8 show alternative embodiments for the utilization of an EMUS-transducer in the inspection of a pipeline.
Figure 8:
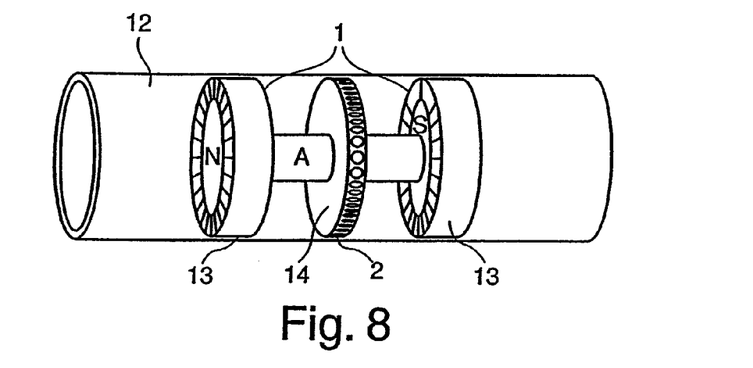

FIGS. 7 and 8 show practical applications of the device of the invention in the field of material testing, particularly for measuring the wall thickness of a material. Pipes that are realized, for example, in the form of pipelines need to be inspected in both instances. For this purpose, the test devices according to FIGS. 7 and 8 need to be combined with a corresponding motive device, for example a so-called pig, in order to move the test devices forward along the pipe.

In order to measure the largest possible surface of the pipe wall, a multitude of individual eddy current coils 2 are arranged between two magnetic poles N, S in the embodiment according to FIG. 7, preferably in the form of a chessboard pattern. The magnetic poles N, S may either be arranged adjacent to one another in the axial direction of the pipe 12 or around the pipe axis in the form of a circular arrangement (see the cross-sectional illustration in FIG. 7). In FIG. 8, the magnetic poles N, S are respectively realized in an annular fashion and connected to one another along a common axis A. The annular or disk-like design of the magnetic poles N, S is respectively adapted to the inside geometry of the pipe 12 to be inspected. Brushes are preferably situated on the circumferential edges of the magnetic poles N, S in order to prevent jamming between the magnet assembly and the inner pipe wall and to realize a cleaning function. A multitude of eddy current coils 2 is provided along the circumferential edge of the disk assembly 14 between both annularly arranged magnetic poles N, S. The disk assembly 14 is rigidly connected to the common magnet axis A that connects both magnetic poles N, S. The transducer illustrated in FIG. 8 is able to measure the entire inner circumference of a pipe section in the axial direction.

The above-described electromagnetic ultrasonic transducer assembly according to the invention therefore combines the following advantages:

The conventional construction of an EMUS-transducer with a magnetization in the immediate proximity of the eddy current coil is replaced, according to the invention, with an assembly in which a substantially larger region of the test object is magnetized with a tangentially extending magnetic field. The distance between the magnetic poles is significantly larger than the dimensions of the eddy current coils.

In such a global magnetization, only the regions of the test object that lie directly underneath the poles are subjected to a magnetic reversal during the movement of the magnet system on the test object. The regions lying between the poles are magnetized almost identically or homogenously in the form of a tangential magnetic field. Consequently, the eddy current coils do not register any interfering signals caused by Barkhausen noise.

It is possible to utilize one or more eddy current coils. The eddy current coils can be positioned at arbitrary locations of the magnetized region of the test object, namely in an arbitrary arrangement. The utilization of several eddy current coils or so-called Coil-Arrays is preferred in the testing of large objects. This makes it possible to achieve high testing speeds without the time-consuming scanning of the test object.

The utilization of one magnetizing unit for several eddy current coils makes it possible to significantly reduce the number of required permanent magnets and to simplify the construction of the EMUS-sensor.

The ultrasonic waves can be emitted at selectable angles by means of a Phased-Array control of several eddy current coils such that it is possible to detect crack-like defects by means of corresponding control equipment.

The stresses on the eddy current coil caused by magnetic forces of attraction that are generated due to the interaction of forces between the magnets and the test object are completely eliminated. This reduces the wear on the probe surface and extends the service life of the EMUS-sensor.

A rigid mechanical connection between the magnet and the eddy current coil can be eliminated. The eddy current coil can be arbitrarily moved over the surface of the test object within the magnetized region. It is possible, in particular, to move the eddy current coil regardless of the surface profile of the test object and to adapt the eddy current coil to uneven areas such as, for example, curvatures, welding seams, etc.

List of Reference Symbols
1 Magnet
2 Eddy current coil
3 EMUS-transducer
4 Test object
5 Engineered surface
6 Free ultrasonic waves
7 Electric conductor
8, 9 Strip conductor section
10 Working zone
11 Cuboid geometry
12 Pipe
13 Brushes
14 Disk assembly

The invention claimed is:

1. A device for the material testing of a test object comprising at least fractions of electrically conductive and ferromagnetic material and at least one engineered surface with at least one electromagnetic ultrasonic transducer assembly that comprises a permanent or electromagnetic assembly with at least two magnetic poles of different magnetic polarity that face the engineered surface, and at least one eddy current coil that projects onto the engineered surface between the two magnetic poles in relation to the engineered surface, and wherein
the permanent or electromagnetic assembly includes a U-shaped magnet body, the magnetic poles of which flatly adjoin the engineered surface, wherein the magnet body extends in a bridge-like fashion over a region of the engineered surface in which the at least one eddy current coil projects or on a surface of which that faces the test object on which the at least one eddy current coil is arranged;

the permanent or electromagnetic assembly at least induces a tangential magnetic field that is oriented parallel to the engineered surface in the test object;

the at least one eddy current coil has a coil geometry that forms a spatially defined region within the test object in which a resultant circuital vector field with a higher eddy current density than the surrounding regions and a uniform eddy current direction is created; and the eddy current direction of the circuital vector field induced in the test object is oriented perpendicular to the magnetic field lines of the tangential magnetic field in the region of the higher eddy current density.

2. A device for the material testing of a test object comprising at least fractions of electrically conductive and ferromagnetic material and at least one engineered surface with at least one electromagnetic ultrasonic transducer assembly comprising a permanent or electromagnetic assembly with at least two magnetic poles of different magnetic polarity that face the engineered surface, as well as at least one eddy current coil that projects on the engineered surface between the two magnetic poles in indirect or direct relation to the engineered surface; and wherein the at least one eddy current coil causes free ultrasonic waves to propagate within the test object perpendicular to the engineered surface which are generated when the eddy current coil is supplied with an alternating current, the permanent or electromagnetic assembly includes two annular magnet bodies that are spaced apart from one another along an axis and respectively have an annular plane, wherein the annular planes perpendicularly intersect the axis and the circumferential edges of the annular planes respectively correspond to a magnetic pole of different magnetic polarization, that at least one eddy current coil is provided between the two magnet bodies and the magnet bodies are integrally connected to one another along the axis.

3. The device according to claim 1, wherein:
the at least one eddy current coil comprises an electric conductor arrangement which is activated by an alternating current and includes at least two electric conductors that substantially extend parallel to one another and through which the alternating current flows in the identical direction.

4. The device according to claim 2, wherein:
the at least one eddy current coil comprises an electric conductor arrangement which is activated by an alternating current and at least regionally or sectionally includes at least two electric conductors that substantially extend parallel to one another and through which the alternating current flows in the identical direction.

5. The device according to claim 3, wherein
the permanent or electromagnetic assembly generates a tangential magnetic field within the test object between the magnetic poles, wherein the tangential magnetic field is substantially oriented parallel to the engineered surface, the electrical conductors substantially extend parallel to one another and perpendicular to the tangential magnetic field and induce an alternating magnetic field $B_{ws}$ within the test object when acted upon by an alternating current which forms a magnetic field B within the test object that can be expressed as follows: $B=BT \pm B_{ws}$.

6. The device according to claim 4, wherein
the permanent or electromagnetic assembly generates a tangential magnetic field within the test object between the magnetic poles, wherein the tangential magnetic field is substantially oriented parallel to the engineered surface, the electrical conductors substantially extend parallel to one another and perpendicular to the tangential magnetic field and induce an alternating magnetic field $B_{ws}$ within the test object when acted upon by an alternating current which forms a magnetic field B within the test object that can be expressed as follows: $B=BT \pm B_{ws}$.

7. The device according to claim 3, wherein
the permanent or electromagnetic assembly generates a tangential magnetic field within the test object between the magnetic poles, wherein the tangential magnetic field is substantially oriented parallel to the engineered surface, and the electrical conductors that substantially extend parallel to one another are perpendicular to the tangential magnetic field and induce eddy currents within the test object when an alternating current is applied thereto, wherein the eddy currents cause generating Lorentz forces that are oriented perpendicular to the engineered surface within the test object in the region of the eddy currents, and longitudinal ultrasonic waves emitted perpendicular to the engineered surface are generated by the Lorentz forces.

8. The device according to claim 4, wherein
the permanent or electromagnetic assembly generates a tangential magnetic field within the test object between the magnetic poles, wherein the tangential magnetic field is substantially oriented parallel to the engineered surface, and the electrical conductors that substantially extend parallel to one another are perpendicular to the tangential magnetic field and induce eddy currents within the test object when an alternating current is applied thereto, wherein the eddy currents cause generating Lorentz forces that are oriented perpendicular to the engineered surface within the test object in the region of the eddy currents, and longitudinal ultrasonic waves emitted perpendicular to the engineered surface are generated by the Lorentz forces.

9. The device according to claim 1, wherein
the eddy current coil includes a three-dimensional body with a real or virtual body core, around the real or virtual body core surface with an electrical conductor being wound in a uniform winding direction; and the three-dimensional body includes a region of the body core surface that is adapted to the engineered surface and in which the conductor includes conductor sections that are located adjacent to one another in a parallel fashion.

10. The device according to claim 2, wherein
the eddy current coil includes a three-dimensional body with a real or virtual body core, around the real or virtual body core surface with an electrical conductor being wound in a uniform winding direction; and the three-dimensional body includes a region of the body core surface that is adapted to the engineered surface and in which the conductor includes conductor sections that are located adjacent to one another in a parallel fashion.

11. The device according to claim 3, wherein
the eddy current coil includes a three-dimensional body with a real or virtual body core, around the real or virtual body core surface with an electrical conductor being wound in a uniform winding direction; and the three-dimensional body includes a region of the body core surface that is adapted to the engineered surface and in which the conductor includes conductor sections that are located adjacent to one another in a parallel fashion.

12. The device according to claim 4, wherein the eddy current coil includes a three-dimensional body with a real or virtual body core, around the real or virtual body core surface with an electrical conductor being wound in a uniform winding direction; and the three-dimensional body includes a region of the body core surface that is adapted to the engineered surface and in which the conductor includes conductor sections that are located adjacent to one another in a parallel fashion.

13. The device according to claim 5, wherein the eddy current coil includes a three-dimensional body with a real or virtual body core, around the real or virtual body core surface with an electrical conductor being wound in a uniform winding direction; and the three-dimensional body includes a region of the body core surface that is adapted to the engineered surface and in which the conductor includes conductor sections that are located adjacent to one another in a parallel fashion.

14. The device according to claim 6, wherein the eddy current coil includes a three-dimensional body with a real or virtual body core, around the real or virtual body core surface with an electrical conductor being wound in a uniform winding direction; and the three-dimensional body includes a region of the body core surface that is adapted to the engineered surface and in which the conductor includes conductor sections that are located adjacent to one another in a parallel fashion.

15. The device according to claim 7, wherein the eddy current coil includes a three-dimensional body with a real or virtual body core, around the real or virtual body core surface with an electrical conductor being wound in a uniform winding direction; and the three-dimensional body includes a region of the body core surface that is adapted to the engineered surface and in which the conductor includes conductor sections that are located adjacent to one another in a parallel fashion.

16. The device according to claim 8, wherein the eddy current coil includes a three-dimensional body with a real or virtual body core, around the real or virtual body core surface with an electrical conductor being wound in a uniform winding direction; and the three-dimensional body includes a region of the body core surface that is adapted to the engineered surface and in which the conductor includes conductor sections that are located adjacent to one another in a parallel fashion.

17. The device according to claim 1, wherein the eddy current coil includes at least two strip conductor sections formed as a rectangular coil; and wherein the rectangular coils are adjacent to one another in one rectangular coil section, through which the alternating current respectively flows in a same direction.

18. The device according to claim 2, wherein the eddy current coil includes at least two strip conductor sections formed as a rectangular coil; and wherein the rectangular coils are adjacent to one another in one rectangular coil section, through which the alternating current respectively flows in a same direction.

19. The device according to claim 3, wherein the eddy current coil includes at least two strip conductor sections formed as a rectangular coil; and wherein the rectangular coils are adjacent to one another in one rectangular coil section, through which the alternating current respectively flows in a same direction.

20. The device according to claim 4, wherein the eddy current coil includes at least two strip conductor sections formed as a rectangular coil; and wherein the rectangular coils are adjacent to one another in one rectangular coil section, through which the alternating current respectively flows in a same direction.

21. The device according to claim 5, wherein the eddy current coil includes at least two strip conductor sections formed as a rectangular coil; and wherein the rectangular coils are adjacent to one another in one rectangular coil section, through which the alternating current respectively flows in a same direction.

22. The device according to claim 6, wherein the eddy current coil includes at least two strip conductor sections formed as a rectangular coil; and wherein the rectangular coils are adjacent to one another in one rectangular coil section, through which the alternating current respectively flows in a same direction.

23. The device according to claim 7, wherein the eddy current coil includes at least two strip conductor sections formed as a rectangular coil; and wherein the rectangular coils are adjacent to one another in one rectangular coil section, through which the alternating current respectively flows in a same direction.

24. The device according to claim 8, wherein the eddy current coil includes at least two strip conductor sections formed as a rectangular coil; and wherein the rectangular coils are adjacent to one another in one rectangular coil section, through which the alternating current respectively flows in a same direction.

25. The device according to claim 9, wherein the eddy current coil includes at least two strip conductor sections formed as a rectangular coil; and wherein the rectangular coils are adjacent to one another in one rectangular coil section, through which the alternating current respectively flows in a same direction.

26. The device according to claim 1, wherein the at least one eddy current coil is mechanically connected to the permanent or electromagnetic assembly so that the at least one eddy current coil is located above the engineered surface without contact or adjoins the engineered surface without substantial force being exerted thereupon.

27. The device according to claim 1, wherein the at least one eddy current coil is located relative to the engineered surface, is independent of the permanent or electromagnetic assembly and is in a manually operated unit.

28. The device according to claim 2, wherein eddy current coils extend along a circumferential edge of an annular or disk-like assembly, a circumferential edge of which is spaced apart from the axis by a distance an identical distance or shorter distance than a spacing of the edge from the axis.

29. A use of the device according to claim 1 comprising measuring the thickness of a test object.

30. The use according to claim 29, wherein a thickness measurement is made using a pulse-echo method in which ultrasonic waves are emitted into the test object in pulsed form perpendicular to the engineered surface and reflected on an opposite surface and wherein a transit time measurement is carried out in which the time of transmission and the time of reception of the ultrasonic waves is measured.

31. The utilization of the device according to claim 1 comprising testing material and/or measuring thickness of pipelines or rail vehicle wheels.

32. A method for the material testing of at least one test object containing at least fractions of electrically conductive and ferromagnetic material by generating electromagnetic ultrasonic waves within the test object having an engineered surface, comprising:

generating a magnetic field $B_T$ within the test object in which the magnetic field lines are at least regionally oriented parallel to the engineered surface and represent a tangential magnetic field;

providing an eddy current coil which is activated with an alternating current relative to the engineered surface in order to induce an alternating magnetic field $B_{ws}$ in the test object that is superimposed with the tangential magnetic field $B_{T\,and}$:

$B=B_T\pm B_{ws}$; and wherein free ultrasonic waves are generated that propagate within the test object perpendicular to the engineered surface by means of magnetostriction and/or Lorentz forces being generated within the test object; and transit times of the ultrasonic waves that freely propagate within the test object are measured, the ultrasonic waves are subject to a reflection event within the test object and return to the location at which they were generated; and the measured transit times are measured as a basis for the material testing.

33. The method according to claim 32, wherein:

field lines of the alternating magnetic field $B_{ws}$ are aligned relative to the tangential magnetic field $B_T$ with an identical or an opposite orientation.

34. The method according to claim 32, wherein:

at least one eddy current coil is activated with an alternating current located relative to the engineered surface in order to induce eddy currents in the test object, such that the induced eddy currents generate Lorentz forces within the test object in superposition with the tangential magnetic field $B_T$, wherein the Lorentz forces stimulate free longitudinal ultrasonic waves that propagate in the test object perpendicular to the engineered surface.

35. The method according to claim 33, wherein:

at least one eddy current coil is activated with an alternating current and is located relative to the engineered surface in order to induce eddy currents in the test object, such that the induced eddy currents generate Lorentz forces $F_L$ within the test object in superposition with the tangential magnetic field $B_T$, so the Lorentz forces stimulate free longitudinal ultrasonic waves that propagate in the test object perpendicular to the engineered surface.

* * * * *